United States Patent [19]

Gold et al.

[11] Patent Number: 4,999,014

[45] Date of Patent: Mar. 12, 1991

[54] METHOD AND APPARATUS FOR MEASURING THICKNESS OF THIN FILMS

[75] Inventors: Nathan Gold, Redwood City; David L. Willenborg, Dublin; Jon Opsal, Livermore; Allan Rosencwaig, Danville, all of Calif.

[73] Assignee: Therma-Wave, Inc., Fremont, Calif.

[21] Appl. No.: 347,812

[22] Filed: May 4, 1989

[51] Int. Cl.$^5$ .......................... G01B 11/06; G01J 4/00
[52] U.S. Cl. ..................................... 356/382; 356/369
[58] Field of Search ................. 356/364, 369, 381, 382

[56] References Cited

U.S. PATENT DOCUMENTS

| | | |
|---|---|---|
| 2,587,282 | 2/1952 | Blodgett . |
| 2,897,371 | 7/1959 | Hasler . |
| 2,973,686 | 3/1961 | Dreyfus et al. . |
| 3,017,512 | 1/1962 | Wolbert . |
| 3,601,492 | 8/1971 | Reichard ............................ 356/108 |
| 3,708,229 | 1/1973 | Pircher ............................... 356/108 |
| 3,737,237 | 6/1973 | Zurasky ............................. 356/161 |
| 3,824,017 | 7/1974 | Galyon ............................... 356/108 |
| 4,293,224 | 10/1981 | Gaston et al. ...................... 356/357 |
| 4,308,586 | 12/1981 | Coates ................................ 364/525 |
| 4,355,903 | 10/1982 | Sandercock ....................... 356/382 |
| 4,358,201 | 11/1982 | Makosch ............................ 356/351 |
| 4,367,044 | 1/1983 | Booth, Jr. et al. ................. 356/357 |
| 4,453,828 | 6/1984 | Hershel et al. .................... 356/382 |
| 4,555,767 | 11/1985 | Case et al. ......................... 364/563 |
| 4,582,431 | 4/1986 | Cole .................................... 356/382 |
| 4,611,919 | 9/1986 | Brooks, Jr. et al. ............... 356/357 |
| 4,618,262 | 10/1986 | Maydan et al. .................... 356/357 |
| 4,645,349 | 2/1987 | Tabata ................................ 356/382 |
| 4,660,979 | 4/1987 | Muething ........................... 356/357 |
| 4,660,980 | 4/1987 | Takabayashi et al. ............. 356/357 |
| 4,672,196 | 6/1987 | Canino ............................... 356/369 |
| 4,744,660 | 5/1988 | Noguchi et al. ................... 356/355 |
| 4,815,856 | 3/1989 | Bruce ................................. 356/357 |
| 4,873,430 | 10/1989 | Juliana et al. ..................... 356/382 |

FOREIGN PATENT DOCUMENTS 0003363   1/1978   Japan .................................. 356/357

OTHER PUBLICATIONS

Hauge, "Optical Film Thickness Measurement Tool", IBM Technical Disclosure Bulletin, vol. 21, #2, Jul. 1978.

Primary Examiner—F. L. Evans
Assistant Examiner—K. P. Hantis
Attorney, Agent, or Firm—Limbach, Limbach & Sutton

[57] ABSTRACT

An apparatus (20) for measuring the thickness of a thin film layer (32) on substrate (28) includes a probe beam of radiation (24) focused substantially normal to the surface of the sample using a high numerical aperture lens (30). The high numerical aperture lens (30) provides a large spread of angles of incidence of the rays within the incident focused beam. A detector (50) measures the intensity across the reflected probe beam as a function of the angle of incidence with respect to the surface of the substrate (28) of various rays within the focused incident probe beam. A processor (52) functions to derive the thickness of the thin film layer based on these angular dependent intensity measurements. This result is achieved by using the angular dependent intensity measurements to solve the layer thickness using variations of the Fresnel equations. The invention is particularly suitable for measuring thin films, such as oxide layers, on silicon semiconductor samples.

44 Claims, 6 Drawing Sheets

METHOD AND APPARATUS FOR MEASURING THICKNESS OF THIN FILMS

TECHNICAL FIELD

The subject invention relates to an apparatus for measuring the thickness of thin films. More specifically, an apparatus is disclosed for precisely determining layer thickness of thin films in a highly localized region.

BACKGROUND

In the prior art, there has been considerable interest in developing methods and apparatus for measuring the thickness of thin films on substrates. This need is particulary acute in the semiconductor manufacturing industry where extremely thin films are deposited on silicon substrates.

One technique which has been developed is classified as ellipsometry. In an ellipsometer, a probe beam, having a known polarization, is directed to reflect off the surface of the sample at an oblique angle. The thickness of the film layer on the substrate will effect the polarization state of the reflected beam. By measuring the polarization state of the reflected beam, information about the thickness of the layer can be derived.

Ellipsometers are quite useful for accurately measuring the thickness of very thin films. However, the spatial resolution of ellipsometers is limited to areas as large as 20-30 microns in diameter. In semiconductor manufacturing, it is often necessary to obtain thickness measurements in a much smaller region, on the order of one micron in diameter. Ellipsometers cannot fulfill this need. Another drawback with ellipsometers is that the range of measurement is quite narrow. While ellipsometers work quite well with extremely thin layers, they become ineffective at thicknesses greater than about 1000 Angstroms.

As noted above, ellipsometers rely on the measurement of the polarization state of a reflected probe beam. An entirely different class of layer thickness measurement devices found in the prior art rely on the interference effects (manifested in changes in surface reflectivity) created when a probe beam is reflected off the sample surface. Where a probe beam wavelength is selected which is at least partially transmitted by the thin film layer, reflections will occur both at the upper surface of the thin film layer and from the upper surface of the substrate. The interaction of the two reflected rays will create interference effects which vary based on layer thickness. These interference effects or changes in surface reflectivity can be detected by measuring the intensity of the reflected beam using a photodetector.

Spectrophotometers are one of the devices within this class of detectors. In a spectrophotometer measurement, the sample is scanned with different wavelengths of light. Since the phase shift through the film is different for each wavelength, each wavelength will undergo different interference effects. By studying the different interference effects created by the different wavelengths, information about the thickness of the thin film layer can be derived. In many spectrophotometers, the wavelength of the probe beam is varied over a significant range to reduce ambiguities in the measurement. Examples of such systems are disclosed in U.S. Pat. No. 3,824,017, issued July 16, 1974 to Gaylon, U.S. Pat. No. 4,293,224, issued Oct. 6, 1981 to Gaston, et al. and U.S. Pat. No. 4,555,766, issued Nov. 26, 1985 to Case, et al.

As described in the Gaston patent, interferometric devices can be used in situ to monitor changing layer thickness during processing. As can be appreciated, as the thickness of the layer changes during a coating operation, interference patterns in the reflected probe beam will change. By monitoring this change in interference patterns, information about the changing layer thickness can be obtained.

In the spectrophotometer techniques discussed above, known variables, such as changes in the wavelength of the probe beam or changes in the thickness of the layer are introduced to gain information about layer thickness. Another type of known variable which can be introduced is a change in the angle of incidence of the probe beam. Interference effects will vary as the angle of incidence the probe beam is changed. One example of a device where the angle of incidence of the input beam is varied can be found in U.S. Pat. No. 4,453,828, issued June 12, 1984 to Hershel, et al.

The latter techniques, which rely on the detection of interference effects, have better spatial resolution than the ellipsometry techniques discussed above. However, even the best interferometric techniques are limited to a resolution of about the 2-3 microns in diameter. More significantly, the interferometric techniques known heretofore are incapable of measuring thin films having a thickness less than 200Å. Finally, the interferometric techniques are not nearly as accurate as the ellipsometer techniques discussed above.

A different interferometric technique is described in U.S. Pat. No. 4,660,980, issued Apr. 28, 1987 to Takabayashi, et al. In this device, a laser beam, which consists primarily of light having S-polarization, is reflected off the surface of the sample at close to Brewster's angle. Assuming the layer is relatively thick, i.e., on the order of 50 microns, a plurality of repeating minima or interference fringes will be produced across the reflected probe beam. In the Takabayashi device, the number of minima or fringes are counted and used to derive information about layer thickness. Takabayashi is therefore limited to measuring relatively thick thin film layers which will generate the multiple fringe effects. In addition, because Takabayashi forces the input beam to have an angle of incidence near Brewster's angle, tight focusing can not be achieved and spatial resolution must be sacrificed.

Accordingly, it would be desirable to provide a new and improved apparatus for measuring the thickness of thin films which is accurate over a wide range of thin film thicknesses.

It is another object of the subject invention to provide an apparatus for measuring thin film thicknesses within a region on the order of 1 micron or less in diameter.

It is still a further object of the subject invention to provide a new and improved apparatus for measuring the thickness of thin films from 50 to 50,000Å.

It is still a further object of the subject invention to provide a new and improved apparatus for measuring thickness of the thin films which utilizes only a single probe beam wavelength.

It is still another object of the subject invention to provide a new and improved apparatus for accurately measuring the thickness of thin film layers which does not require any means for actively changing the incidence angle of the probe beam.

It is still another object of the subject invention to provide a new and improved apparatus for measuring the thickness of a thin film layer which does not have to be operated in situ, where the thickness of the thin film is changing.

It is still a further object of the subject invention to provide a new and improved apparatus which is capable of determining the refractive index of a thin film as well as the thickness of the thin film layer.

It is a further object of the subject invention to provide a method for refining the accuracy of the thin film thickness measurement by providing an additional detector for recording the total power of the reflected probe beam.

SUMMARY OF THE INVENTION

In accordance with these and many other objects, the subject invention provides for a new and improved method and apparatus for measuring the thickness of thin film layers deposited on a substrate. The apparatus is particularly suited for measuring layer thicknesses deposited on the silicon substrates found in the semiconductor industry.

The apparatus includes a means for generating a probe beam of radiation having a single wavelength. In the preferred embodiment, a laser is utilized to generate the beam because it provides accurate wavelength information, can be tightly focused, and has enough power to accurately allow measurement of the reflectivity. The laser beam is focused substantially normal to the surface of the sample using a high numerical aperture lens. The high numerical aperture lens allows focusing to a spot diameter of about 1 micron. In accordance with the subject invention, the use of the high numerical aperture lens also creates a ray pattern within the incident focused beam having a wide range of angles of incidence with respect to the surface of the sample. Information derived from various rays having different angles of incidence within the focused probe beam can be used to derive information about layer thickness.

The latter result is achieved by measuring the intensity variations across the reflected probe beam as a function of the angle of incidence of the various rays within the focused incident probe beam. The angle of incidence of the rays within the focused probe beam with respect to the surface of the sample is related to the position of the rays in the reflected probe beam. More specifically, the ray in the center of the reflected probe beam will correspond to the center ray in the incident beam. Assuming the probe beam is focused normal to the surface of sample, the center ray will have an incidence angle of 0°. In contrast, the portions of the reflected probe beam at the outer edges thereof correspond to the highest angles of incidence. The highest angle of incidence is dependent on the focusing power or numerical aperture of the lens. The maximum angle $\theta_m$ is given by the following equation:

$$\text{Sine } \theta_m = (\text{numerical aperture}) \qquad (1)$$

The location of any ray in the reflected probe beam corresponds to the sine of the angle of incidence of the associated ray in the focused incident probe beam.

As is known from the prior art patents discussed above, if measurements can be made over varying angles of incidence, information about layer thickness can be derived. This result is a consequence of the fact that the interference effects vary for different angles of incidence. The interference effects (or changes in surface reflectivity) can be seen as changes of the intensity across the reflected probe beam. The expected reflectance of linear polarized light from a thin film substrate of a given thickness can be calculated using Fresnel's equations. Thus, the angular dependent intensity measurements can be compared to expected values derived from the Fresnel equations to give information about the thickness of the thin film layer.

In the preferred embodiment, the light in the probe beam is initially linearly polarized such that when it is tightly focused normal to the surface of the sample, the incident rays will have substantial components of S and P polarized light relative to the sample surface. The detector means comprises 2 orthogonal arrays, oriented in a manner to isolate and detect the interference effects from the S and P polarized components of the incident beam. By measuring angular dependent intensity profiles for each of the polarizations states, measurement ambiguity is reduced and accuracy is improved.

In addition to improving accuracy, information about the reflectance of the isolated P-polarized light near Brewster's angle can be used to derive information as to the refractive index of either the thin film layer or the substrate. As noted above, the use of a high numerical aperture lens will generate a relatively large spread of incidence angles in the rays of the focused incident probe beam. In the preferred embodiment, the incidence angles will include not only the normal but rays at Brewster's angle. At Brewster's angle, the intensity of the reflected P polarized light does not vary significantly with changes in layer thickness. Therefore, a measurement of the reflectivity of rays incident at or about Brewster's angle can give information about the index of refraction of either the substrate or the thin film layer.

The subject apparatus is capable of making thickness measurements over a wide range of thin film thicknesses. It is believed this system will provide information for layers ranging from 50Å to 50,000Å. Equally significant is the fact that a spatial resolution on the order of 1 micron in diameter can be achieved. In this manner, highly localized thickness measurements can be made over a broad range of layer thicknesses.

The accuracy of measurement of layer thickness can be enhanced if the total reflected power of the probe beam is also measured. More specifically, it is known that the reflectivity of the surface of the sample will vary approximately sinusoidally with the thickness of the thin film layer. However, information about layer thickness cannot be derived from this measurement alone since any particular reflectivity measurement would be consistent with a number of different layer thickness. These ambiguities can be removed if a very good approximation of layer thickness is first made using the device described above. Once this measurement is made, data taken from a reflectivity measurement based on the total power of the reflected beam can be used to reduce the uncertainty in layer thickness even further. This added sensitivity is a result of the fact that the signal to noise ratio of the measurement of the full power of the beam will be much better than the initial detector measurement where only portions of the beam, at discrete points corresponding to specific angles of incidence, are measured.

Further objects and advantages of the subject invention will be apparent from the following detailed description taken in conjunction with the drawings in which:

DETAILED DESCRIPTION OF THE PREFERRED EMBODIMENTS

Figure 1:
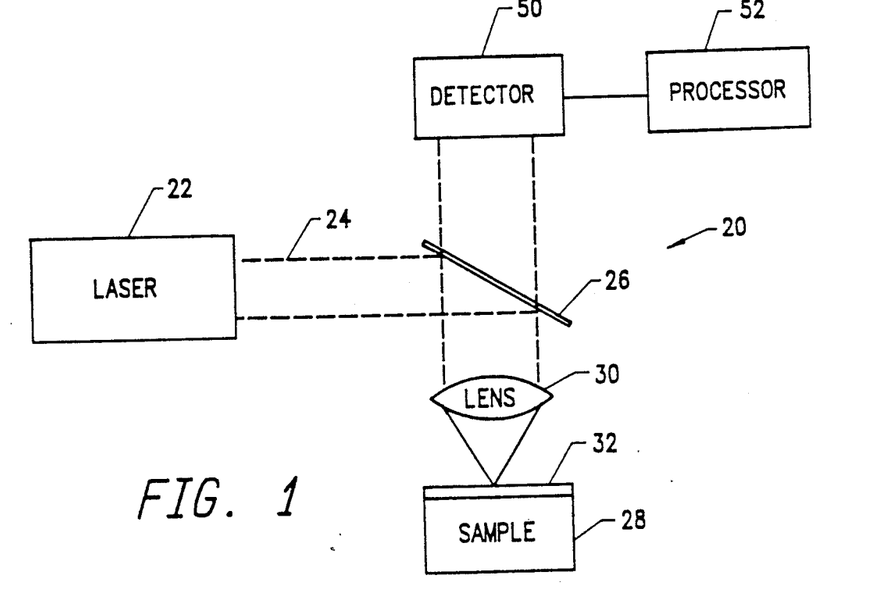
FIG. 1 is a simplified block diagram of the apparatus of the subject invention.

Referring to FIG. 1, there is illustrated, in schematic form, the basic apparatus 20 for carrying out the method of the subject invention. Apparatus 20 includes a laser 22 for generating a probe beam of radiation 24. Probe beam 24 is reflected downward by a beam splitter 26 towards the sample 28 having a thin film layer 32 deposited thereon. In accordance with the subject invention, beam 24 is focused on the surface of the sample 28 with a high numerical aperture lens 30. Preferably, beam 24 is focused substantially normal to the surface of the sample in order to minimize the spot size and maximize resolution.

Figures 2, 3:
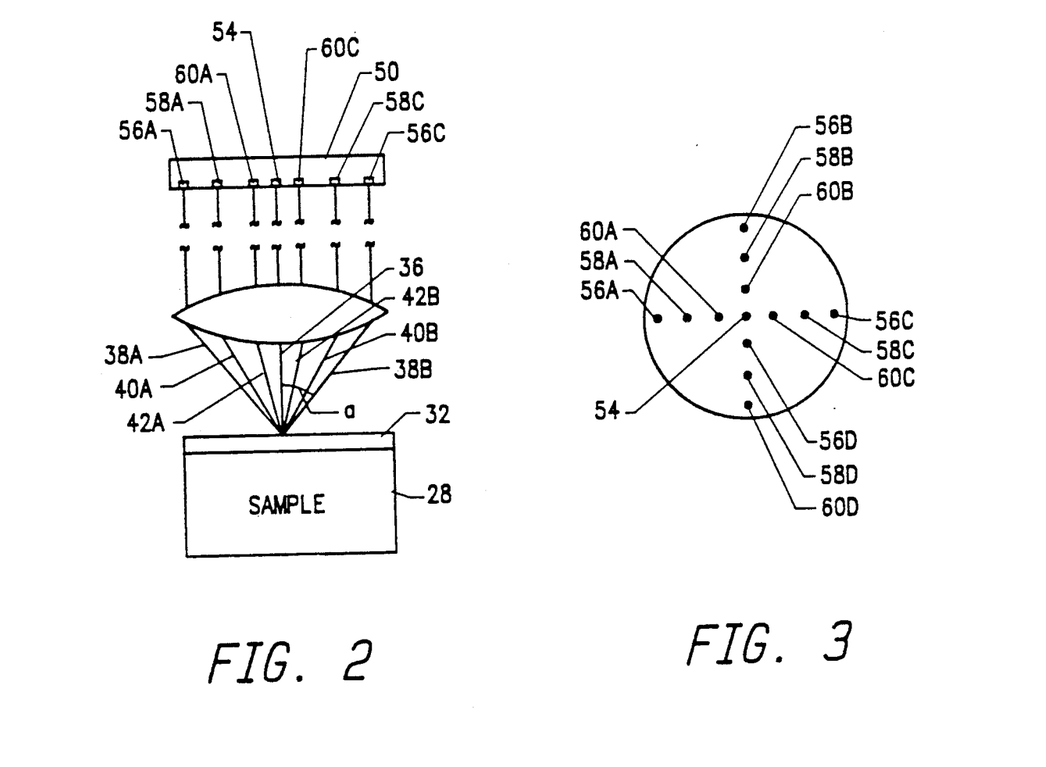
FIG. 2 is a diagram of the focusing of the probe beam, enlarged with respect to FIG. 1.
FIG. 3 is a plan view of the surface of a photodetector which can be used to carry out the method of the subject invention.

FIG. 2 is an enlarged view of the probe beam 24 shown focused onto the sample 28 by lens 30 and illustrating some of the individual rays within the incident focused probe beam. As can be seen, where beam 24 is directed normal to the surface, the incident focused beam will include a center ray 36 substantially normal to the surface of the sample. The focused beam will also include outer rays, 38A and B, having a maximum angle (a) of incidence with respect to the surface of the sample. As set forth in equation (1) above, the angle of incidence of the outer rays 38 is dependent upon the numerical aperture of lens 30. Intermediate rays have angles of incidence proportional thereto. For example, symmetric rays 40A and 40B illustrate an angle of incidence of 30° while symmetric rays 42A and 42B represent an angle of incidence of 15°.

Lens 30 is selected to have a high numerical aperture thereby maximizing the spread of angles of incidence. In practice, a lens creating a spread of angles (from the center ray to the outermost ray) of at least 30° is desired. A lens having a numerical aperture of 0.5 will provide such a spread of rays. In the preferred embodiment, a lens having a 0.95 numerical aperture is used which gives a spread of greater than 70°.

After reaching the sample, beam 24 is reflected back upwardly through lens 30, past beam splitter 26 and falls on photodetector 50. The surface of photodetector 50 is shown in FIG. 3. Photodetector 50 includes a plurality of individual discrete detecting elements, the outputs of which are supplied to processor 52.

In accordance with the subject invention, detector 50 and processor 52 function to measure the intensity of the reflected probe beam as a function of the angle of incidence of various rays within the focused incident probe beam. This result can be appreciated through an optical pathway analysis illustrated in FIGS. 2 and 3. As can be seen, center element 54 of detector 50 will receive and measure the light intensity of the ray 36 passing through the center of lens 30. Accordingly the output of detector element 54 would correspond to a ray having an angle of incidence of zero degrees. Similarly, the radially outer elements 56A-D on detector 50 receive and measure the light intensity of rays 38A and 38B, which have the greatest angle of incidence. As noted above, this angle of incidence is known based upon the numerical aperture of lens 30. Discrete elements 58A-D and 60A-D correspond to angles of incidence between zero and the highest angle. In the illustrated embodiment, elements 58A-D are located in a manner to receive and measure rays 38A-D having an angle of incidence of 30° while discrete elements 60A-D are located in a manner to receive and measure rays 42A-D having an angle of incidence of 15°.

The detector surface shown in FIG. 3 illustrates only a few discrete detecting elements. As can be appreciated, additional information can be obtained by increasing the number of detecting elements in a manner to gain information with respect to a larger number of discrete angles of incidence of the focused probe beam. For example, additional elements could be used to measure other angles of incidence.

In the embodiment illustrated in FIGS. 2 and 3, two arrays of detector elements, oriented orthogonally with respect to each, are provided. Two orthogonally disposed arrays of detector elements are desirable in order to isolate information about S and P polarized light as discussed below.

In the preferred embodiment, probe beam 24 consists of linearly polarized light normally incident onto the sample surface. When the normally incident, linearly polarized light is tightly focused by lens 30, the light rays incident on the sample surface will have substantial components of S and P polarized light with respect to the sample surface. Light which is substantially all S polarized will lie along one axis. Conversely, light which is substantially all P polarized will lie along another axis, orthogonal to the first. Axes between these two orthogonal axes will contain a mixture of both components.

It has been found that if two orthogonal arrays of detectors, as shown in FIG. 3, are properly oriented, the S and P polarization components can be isolated from the probe beam. The isolated S and P-polarization intensity information can be used to calculate the thickness of the thin film layer on a sample as well as to derive information about the index of refraction of the sample as discussed in greater detail below.

Figure 4A:
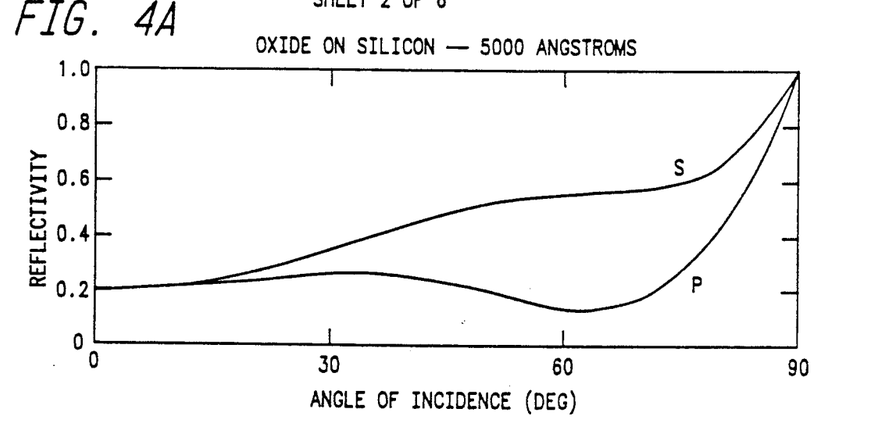
FIGS. 4A-C include three graphs plotting the reflectivity of S and P polarized light with respect to the angle of incidence of the incoming probe beam at three different thickness levels of an oxide on a silicon wafer.
Figure 4B:
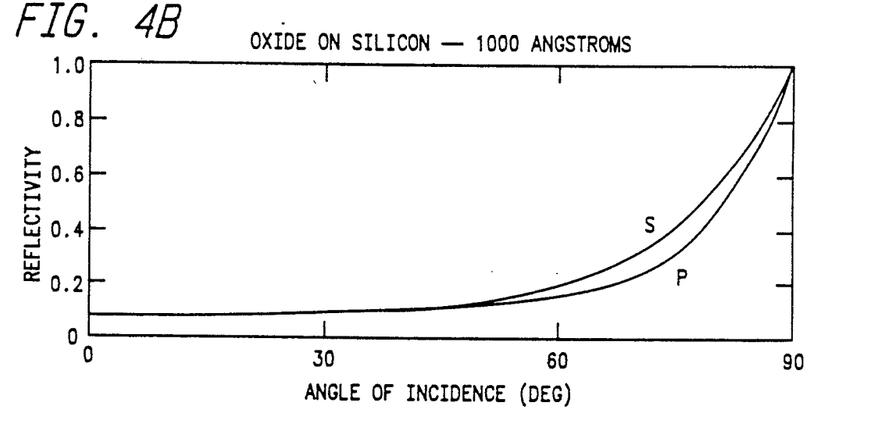
Figure 4C:
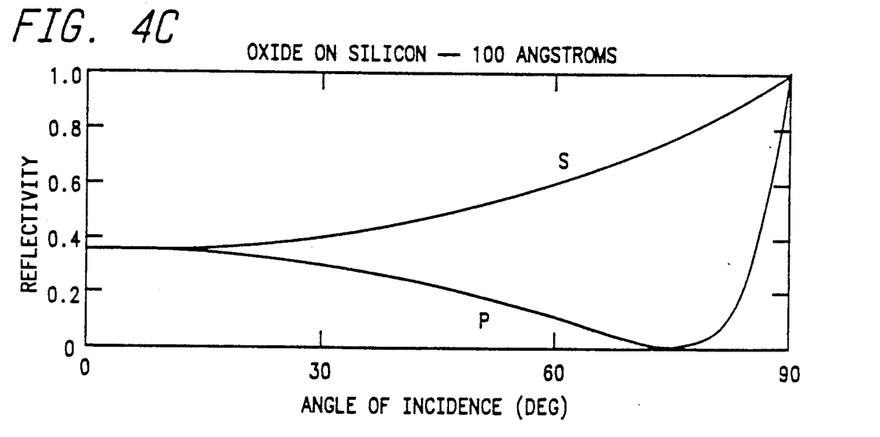

FIGS. 4A-C illustrate the type of measurements which might be generated with an apparatus 20 of the subject invention. Each of the graphs illustrates the reflectivity of the surface of the sample for the S and P polarized light as a function of the angle of incidence in degrees. The reflectivity of the sample is proportional to the intensity of the reflected probe beam which is directly measured by the discrete elements on the photodetector 50. A measurement of surface reflectivity of the surface is derived by calibrating the output of the photodetector. FIGS. 4A-4C illustrate reflectivity curves for an oxide layer on a silicon semiconductor substrate taken with thin film oxide layers of 5,000 angstroms, 1,000 angstroms and 100 angstroms thick. As can be seen, the reflection curves are substantially different for each of the different layer thicknesses. This information can therefore be used to derive information about layer thickness.

Information about layer thickness is specifically derived using the measured reflectance information in a mathematical model or set of equations which relate reflectivity, angle of incidence and layer thickness. The equations utilized are based on the well known Fresnel equations. The principal equation for the reflectivity of a sample with respect to S polarized light is as follows:

$$R = \frac{r_L + r_S + 2\sqrt{r_L r_S} \cos(2 k_1 t)}{1 + r_L r_S + 2\sqrt{r_L r_S} \cos(2 k_1 t)} \quad (2)$$

where R is the reflectivity of the light derived from the isolated intensity measurement, the index of refraction in air is taken as one and t is the thickness of the layer. The constant k in equation (2) is given by the formula:

$$k_1 = \frac{2\pi}{\lambda} n_L \cos \theta_L \quad (3)$$

where $\lambda$ is the wavelength of the probe beam. All r values are for the reflectivity of polarized light where $r_L$ is the reflectance from the surface of thin film layer and $r_S$ is the reflectance from the surface of the substrate.

For S polarized light, the reflectivity from the surface thin film layer ($r_L$) and the substrate ($r_S$) are given by the following equations:

$$r_L = \left( \frac{n_L \cos \theta_L - \cos \theta_O}{n_L \cos \theta_L + \cos \theta_O} \right)^2 \quad (4)$$

and $$r_S = \left( \frac{n_S \cos \theta_S - n_L \cos \theta_L}{n_S \cos \theta_S + n_L \cos \theta_L} \right)^2 \quad (5)$$

where $n_L$ is the index of refraction of the thin film layer, $n_S$ is the index of refraction of the substrate, $\theta_O$ is the angle of incidence at the interface between the air and surface of the thin film layer, $\theta_L$ is the angle of incidence in the thin film layer and $\theta_S$ is the angle of incidence in the substrate.

For P polarized light, the reflectivity from the surface of the thin film layer ($r_L$) and the substrate ($r_S$) is given by the following equations:

$$r_L = \left( \frac{\frac{n_L}{\cos \theta_L} - \frac{1}{\cos \theta_O}}{\frac{n_L}{\cos \theta_L} + \frac{1}{\cos \theta_O}} \right)^2 \quad (6)$$

and $$r_S = \left( \frac{\frac{n_S}{\cos \theta_S} - \frac{n_L}{\cos \theta_L}}{\frac{n_S}{\cos \theta_S} + \frac{n_L}{\cos \theta_L}} \right)^2 \quad (7)$$

Figure 5:
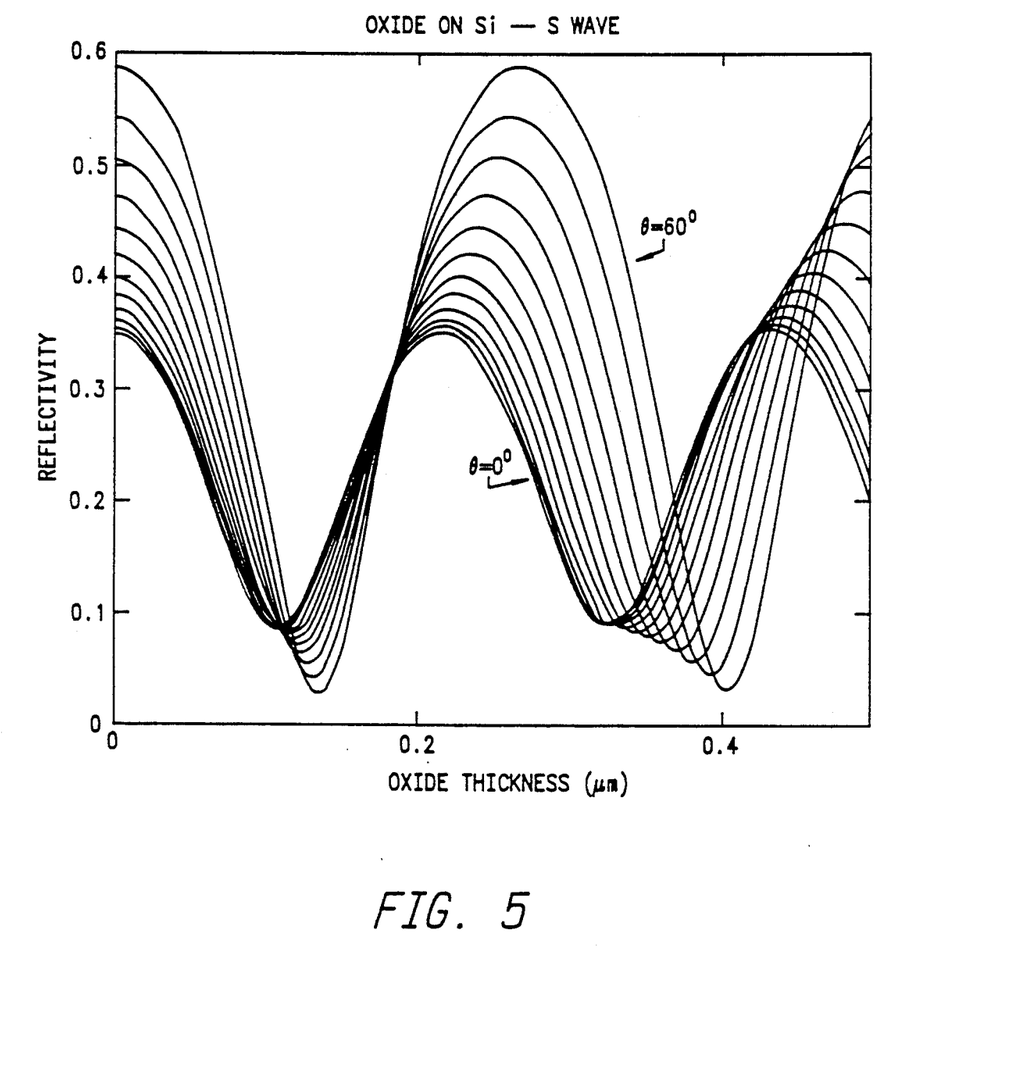
FIG. 5 illustrates the variation of reflectivity of S-polarized light in a focused incident probe beam with respect to different oxide thicknesses on silicon at various angles of incidence.
Figure 6:
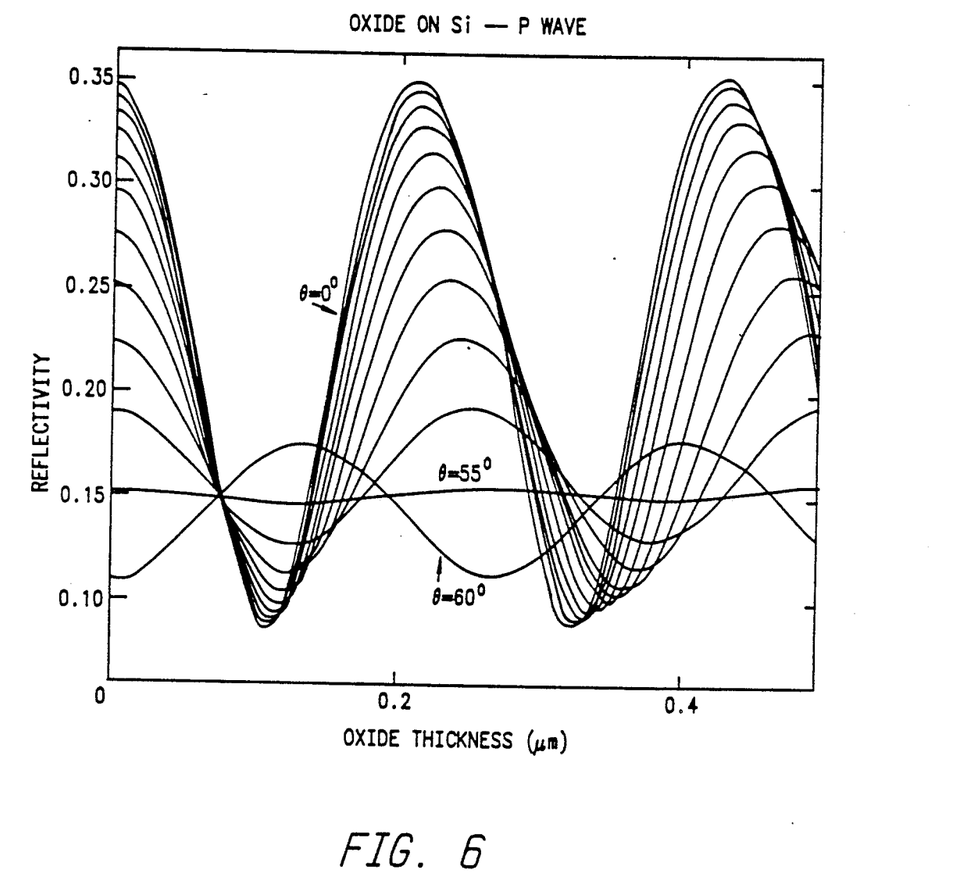
FIG. 6 illustrates variations of reflectivity of P-polarized light in a focused incident probe beam as a function of different thickness on silicon at various angles of incidence.

FIGS. 5 and 6 are computer generated graphs of reflectance curves for the S and P polarized light generated using the equations set forth above. The multiple curves in each of the graph represent angles of incidence ($\theta$) from 0° to 60° in 5° increments. The graphs demonstrate how reflectivity varies with oxide thickness.

Figures 7, 8:
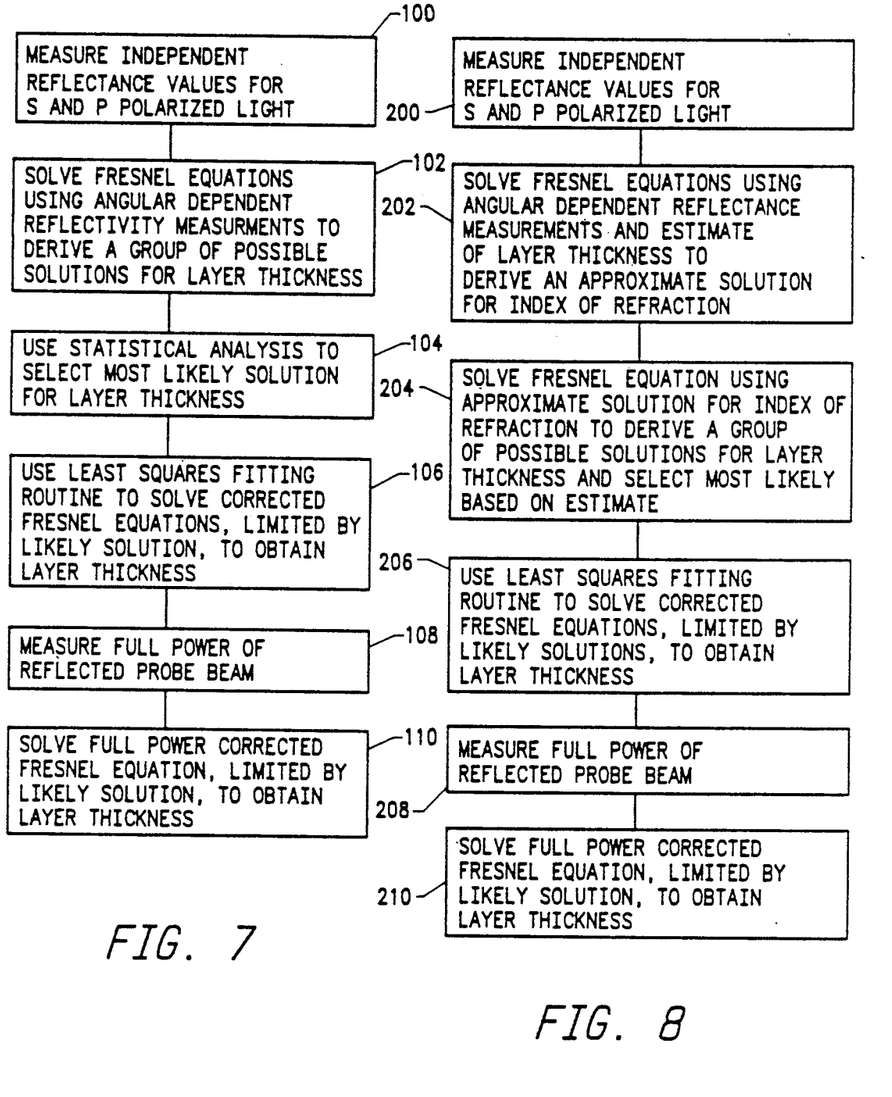
FIG. 7 is a flow chart illustrating the steps the processor takes to derive layer thickness in accordance with the subject invention.
FIG. 8 is a flow chart illustrating the steps the processor takes to derive both layer thickness and index of refraction in accordance with the subject invention.

FIG. 7 is a flow chart of the algorithm the processor uses to derive the thickness of a thin film layer based upon the measured reflectance values that are a function of the angle of incidence. The measured reflectance values are obtained in step 100 by apparatus 20 as discussed. In step 102, the processor solves equation (2) using the measured reflectance values and the substitutions from equations (4) through (7). As should be clear from FIGS. 5 and 6, any particular reflectively measurement will correspond to a number of different layer thicknesses. Thus, the result in step 102 will include a number of possible solutions for the thickness of the thin film. In step 104, a statistical analysis is performed to select a single, most likely solution for layer thickness from the group of solutions derived in step 104. This solution will typically be accurate to within 20 angstroms.

The accuracy of the result can be further improved if an analysis is made which takes into account such factors as light absorption by the sample and the effect of a finite detector size. The amount of absorption varies from material to material. If the materials are known, various correction factors can be incorporated into equation (2) to further refine the determination. However, such correction factors make an analytical solution of the equations difficult. Thus, a numerical solution must be sought using a least squares fitting routine as set forth in step 106. Such a numerical analysis is greatly facilitated due to the fact that an approximate solution for layer thickness has already been determined. Thus, in step 106, a least squares fitting routine is used to solve a set of Fresnel equations, corrected for absorption characteristics of the particular sample being tested and limited by the likely solution for layer thickness obtained in step 104. If the solution is refined in this manner, the accuracy of the measurement can be significantly improved. This measurement can be made on films ranging in thickness from 50 angstroms to 50,000 angstroms with a spatial resolution on the order of 1 micron.

In many situations, in particular thin films having a thicknesses less than 1000 angstroms, there is a need to know the thickness with even greater accuracy. In accordance with the subject invention, greater accuracy can be achieved by making an additional measurement of the total power of the reflected probe beam as shown in step 108. As will be discussed below with reference to FIG. 9, this measurement is preferably made by using a separate photodetector. However, an approximation of this measurement could be made by adding the outputs of all of the discrete elements 54 through 60 of the detector shown in FIG. 3. Assuming that the detector is underfilled by the beam (i.e., the entire reflected beam falls within the confines of the detector elements) a measurement proportional to the total power of the beam can be made.

The analysis of layer thickness based on this additional information is similar to that stated above. More specifically, equation (2) is modified by the substitutions set forth below in order to relate layer thickness to the reflectance of the full beam from the thin film layer (L) and substrate (S).

$$r_L = \frac{n_L - 1}{n_L + 1} \quad (8)$$

$$r_S = \frac{n_S - n_L}{n_S + n_L} \quad (9)$$

$$K_1 = \frac{2\pi n_L}{\langle\lambda\rangle} \quad (10)$$

where $\langle\lambda\rangle$ is an effective wavelength, slightly greater than $\lambda$, which accounts for the 3-dimensional beam spreading of the focused beam within the layer.

When comparing layer thickness to reflectivity based on the latter equations, one finds that the curve is highly sinusoidal giving a large number of possible thickness solutions for any given measurement of total reflected power. This problem is overcome if the thickness of the thin film layer is first established to within a narrow range in step 106. This information reduces the possible solutions of the latter modified Fresnel equations so that the measurement of the total reflected power of the beam derived in step 108 can now be used to refine the calculation of layer thickness to a much greater degree of accuracy in step 110.

The reason the full power measurement provides greater accuracy is that the signal to noise ratio of the measurement is on the order of 10 to 100 times better than the measurement of any of the discrete elements on detector 50. As can be appreciated, the reflected beam is spread out over the surface of the detector such that any of the discrete elements will receive only a fraction of the power of the beam and thus be sensitive to beam shape and beam position fluctuations. In contrast, the full power measurement takes advantage of the full laser power and thus is much less sensitive to small beam shape and beam position fluctuations.

In another aspect of the subject invention, the index of refraction of either the thin film layer or the substrate can be calculated along with the thickness of the thin film layer. This capability is a result of the fact that the high numerical aperture lens can be used to create rays having an angle of incidence at or near Brewster's angle. Referring to FIG. 6, it will be seen that the reflectance of the sample with respect to P-polarized light varies quite significantly with changes in oxide thickness for virtually all of the angles of incidence. However, as the angle of incidence approaches Brewster's angle, ($\theta$ equals about 55°96 for silicon dioxide) the reflectivity curve becomes almost flat. Thus, the reflectivity measurement of P-polarized light at Brewster's angle is substantially independent of layer thickness. However, reflectivity will vary with changes in the index of refraction of either the layer or substrate.

An algorithm for deriving layer thickness and the index of refraction of either the substrate or the thin film layer is shown in FIG. 8. This approach assumes that the layer thickness is known within some range and that the index of refraction of either the substrate or thin film layer is known.

As set forth in step 200, reflectance measurements are made, including a measurement of P-polarized light at Brewster's angle. In step 202, an approximate solution for the unknown index of refraction (either of the substrate or of the thin film layer) can be calculated using equations (2), (6) and (7) and an estimated layer thickness. Using the approximate solution for the index of refraction, a group of solutions for the actual thickness of the thin film layer is calculated in step 204 using equation (2) and an approach identical to Step 102 in FIG. 7. From these possible solutions, one solution is selected based on the fact that there is some prior knowledge of a thickness range. Using the calculated approximate thickness and calculated approximate index of refraction, a least squares fitting routine is used with the Fresnel equations, corrected for absorption and detector size, to generate the best solution for layer thickness and index of refraction in step 206 (as in Step 106 in FIG. 7).

As noted above, the accuracy of the thickness measurement of the thin film can be further enhanced by taking a measurement of the full power of the reflected probe beam in step 208. This measurement is used to calculate layer thickness in step 208 using equation (2) (as modified by equations 8–10) and limited by the solution for layer thickness calculated in step 206.

Figure 9:
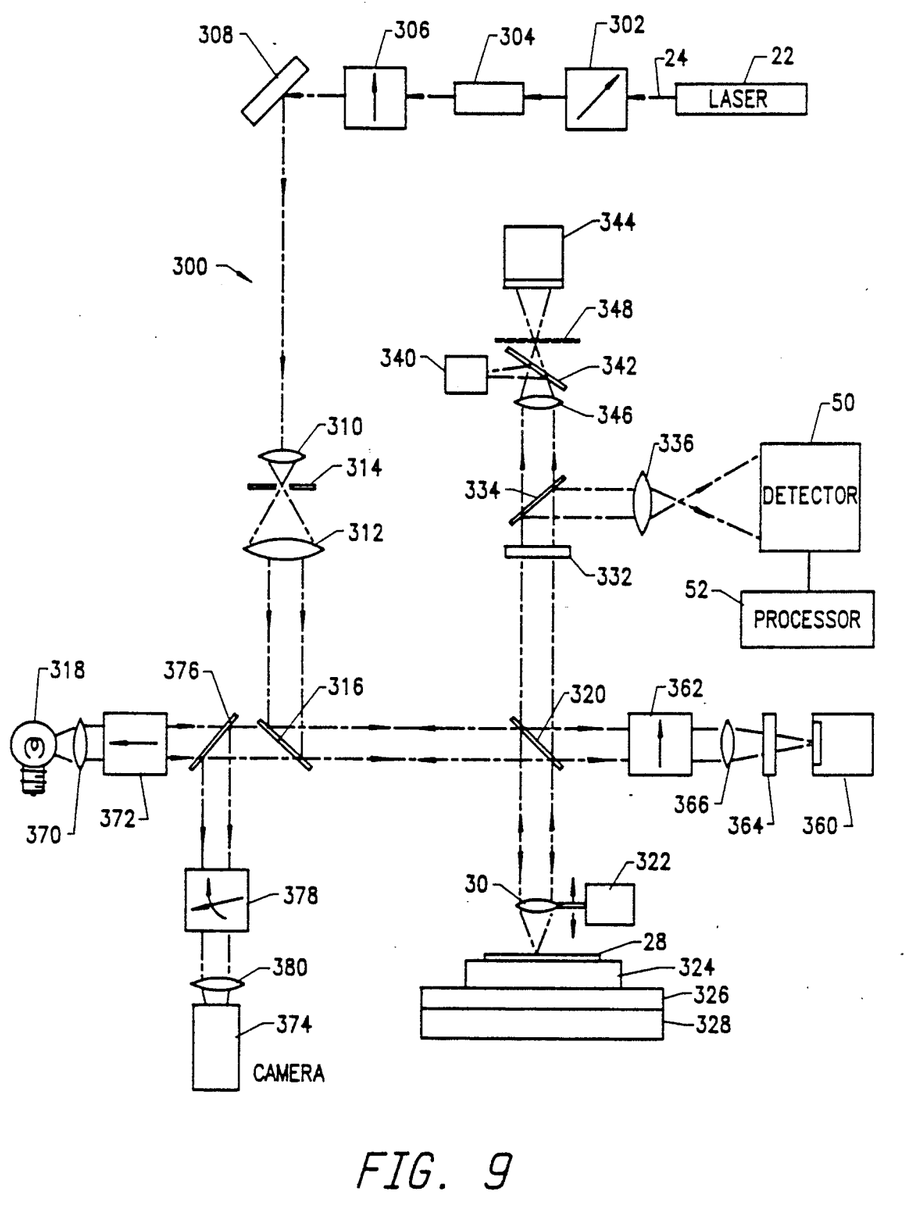
FIG. 9 is a schematic diagram of the preferred embodiment of the subject invention.

Having described the basic theory and operation of the subject's invention, one preferred apparatus 300 for carrying out the measurements will be described with reference to FIG. 9. In FIG. 9, parts equivalent to the structure shown in FIG. 1 are numbered the same.

As noted above, laser 22 generates an output beam 24. Laser 22 can be a helium neon laser having a 5 milliwatt power output and a polarization oriented at 45°. Beam 24 is then passed through a polarizing filter 302 oriented at 45° to insure only 45° polarized light is transmitted. This light is then passed through a faraday rotator 304 for rotating the polarization an additional 45° to prevent spurious reflected helium neon radiation from being reflected back into the helium neon laser. This arrangement reduces instabilities in the power output of the laser caused by spurious reflected HeNe radiation. Beam 24 is them passed through a polarizing filter 306 oriented at 90° to further reduce spurious reflected radiation from going back into the laser.

The beam 24 is then reflected downward by a metallic coated glass turning mirror 308 and down into a beam expander spatial filter arrangement. This arrangement includes an input lens 310 and an output lens 312. A pin-hole filter 314 is provided to improve the beam profile and its uniformity. The beam that exits lens 312 is expanded by the ratio of the focal length of lens 310 and lens 312.

The beam is then turned with a metallic coated glass beam splitter 316 having an 20% transmission and 80% reflection. This beam splitter is used to combine the HeNe beam and white light from source 318. The white light is used to image the sample using a vision system described in greater detail below.

The probe beam is then directed downward towards the sample by a metallic coated glass beam splitter 320 having a 60% transmission and 40% reflection. This same beam splitter also functions to turn the white light down towards the sample. Upon return from the sample, part of the probe beam passes up through the splitter 320 and will be collected by the detector 50. Some of the white light from source 318 will be reflected back to the vision system.

The probe beam is focused on the sample through the objective lens 30. Lens 30 has a high numerical aperture so the various rays in the focused beam will have a wide spread of angles of incidence. The position of lens 30 is controlled by an autofocus mechanism 322. As noted above, beam 24 is focused to a spot size about 1 micron in diameter on the surface of sample 28. The sample 28, which may be a silicon semiconductor with a thin film oxide layer, is mounted on a stage which provides X, Y and rotational positional movement. The top stage 324 provides rotational movement as well as a vacuum chuck for holding down the wafer. Stages 326 and 328 provide X and Y linear movement.

Light from the HeNe probe beam and white light that is reflected from the sample passes through beam splitter 320. The transmission of white light is restricted by a band pass filter 332 which transmits only the 633 nm HeNe wavelength radiation. A portion of the HeNe probe beam is then redirected by a metallic coated glass beam splitter 334 to detector 50. Beam splitter 334 has a 20% transmission and an 80% reflection. The reflected light from beam splitter 334 is expanded by lens 336 and imaged on detector 50 which was described above with reference to FIG. 1. Detector 50 can be defined by a diode array, CCD camera, scanning pin-hole or fiber optic sensor array. Preferably, detector 50 has detector elements which are arranged to isolate the information from about the reflectivity of the S and P polarization light incident on the surface of the sample. The output of detector 50 is supplied to the processor 52.

As mentioned above, the accuracy of the thickness measurement can be further enhanced by measuring the full power of the reflected probe beam. In the embodiment illustrated in FIG. 9, a separate detector 340 is provided for that purpose. A portion of the probe beam is directed to the detector 340 by metallic coated glass beam splitter 342. The only requirement of detector 340 is that the probe beam substantially underfill the detecting surface so that the full power of the beam can be measured.

In the illustrated embodiment, an autofocus mechanism is provided. Autofocus mechanism comprises a bi-cell photo detector 344, lens 346 and a chopper wheel 348. Autofocusing using these types of components is known in the art.

In order to insure proper calibration, the output power of the laser 22 must be monitored. This result is achieved using a detector 360 upon which a part of the probe laser beam 24 is directed. A polarizing filter 362 and a band pass filter 364 removes white light from the HeNe probe beam. Lens 366 is used to image the beam onto detector 360.

In the illustrated embodiment, apparatus 300 includes a vision system to allow the operator to locate points on the sample. The vision system includes a white light source 318, collimating lens 370 and polarizing filter 372. Polarizing filter 372 is designed to polarize the white light perpendicular to the polarization state of the probe beam thus allowing separation of the white light and the helium neon beams by the downstream optics.

A portion of the white light returning from the sample is directed downward to a camera 374 by a 50/50 beam splitter 376. A tunable polarization filter 378 is provided to control the amount of probe beam radiation falling on the video camera 374. Lens 380 focuses the image provided for the camera.

The basic operation of the apparatus 300 is the same as set forth above with respect to FIGS. 1-3. The detector 50 and processor 52 function to measure the intensity of the reflected probe beam as a function of the angle of incidence of the rays in the incident focused probe beam. Calculations of layer thickness are performed using the equations and algorithms discussed above.

In summary, there has been provided a new and improved method and apparatus for measuring the thickness of a thin film layer on a substrate. In a preferred embodiment, a probe beam of radiation is focused substantially normal to the surface of the sample using a high numerical aperture lens. A high numerical aperture lens provides a large spread of angles of incidence of the rays within the incident focused beam. A detector is provided for measuring the intensity across the reflected probe beam as a function of the angle of incidence with respect to the surface of the substrate of various rays within the focused incident probe beam. A processor functions to derive the thickness of the thin film layer based on these angular dependent intensity measurements. This result is achieved by using the angular dependent intensity measurements to solve the layer thickness using variations of the Fresnel equations.

In one embodiment, the focused probe beam includes substantial components of S and P polarized light. In addition, the detector is designed to isolate the S and P polarized components to facilitate evaluation of layer thickness. Preferably, an additional detector is provided for measuring the full power of the reflected probe beam. The additional signal information provided from the latter detector is used to refine the accuracy of the derived thickness measurement.

While the subject invention has been described with reference to the preferred embodiments, various other changes and modifications could be made therein by one skilled in the art without varying from the scope or spirit of the subject invention as defined by the appended claims.

We claim:

1. An apparatus for measuring the thickness of a thin film layer on the surface of a substrate comprising:

means for generating a probe beam of radiation;

means for focusing said probe beam substantially normal onto the surface of the substrate such that various rays within the focused probe beam create a spread of angles of incidence with respect to said surface;

detector means for receiving the probe beam after it has been reflected from the surface of the substrate, said detector means for measuring the intensity of various rays as a function of position with the reflected probe beam, with the position of the rays within said reflected probe beam corresponding to specific angles of incidence with respect to said surface; and processor means for determining the thickness of the thin film layer based upon the angular dependent intensity measurements made by the detector means.

2. An apparatus for measuring the thickness of a thin film layer on the surface of a substrate comprising:
means for generating a probe beam of radiation;
means for focusing said probe beam onto the surface of the substrate such that various rays within the focused probe beam create a spread of angles of incidence with respect to said surface and wherein said focused incident probe beam includes at least one ray substantially normal to the surface of the substrate;
detector means for receiving the probe beam after it has been reflected from the surface of the substrate, said detector means for measuring the intensity of various rays as a function of position within the reflected probe beam, with the position of the rays within said reflected probe beam corresponding to specific angles of incidence with respect to said surface; and
processor means for determining the thickness of the thin film layer based upon the angular dependent intensity measurements made by the detector means.

3. An apparatus as recited in claim 1 or 2 wherein said focused incident probe beam includes at least one ray inclined near Brewster's angle with respect to either the thin film layer or the substrate.

4. An apparatus for measuring the thickness of a thin film layer on the surface of a substrate comprising:
means for generating a probe beam of radiation;
means for focusing said probe beam onto the surface of the substrate such that various rays within the focused probe beam create a spread of angles of incidence with respect to said surface, wherein said focusing means is defined by a lens having a numerical aperture of at least 0.5;
detector means for receiving the probe beam after it has been reflected from the surface of the substrate, said detector means for measuring the intensity of various rays as a function of position within the reflected probe beam, with the position of the rays within said reflected probe beam corresponding to specific angles of incidence with respect to said surface; and
a processor means for determining the thickness of the thin film layer based upon the angular dependent intensity measurements made by the detector means.

5. An apparatus for measuring the thickness of a thin film layer on the surface of a substrate comprising:
means for generating a probe beam of radiation;
means for focusing said probe beam onto the surface of the substrate such that various rays within the focused probe beam create a spread of angles of incidence with respect to said surface, wherein the variation in the angle of incidence of the rays of the focused incident probe beam, from the center to the outer edge, is at least 30 degrees;
detector means for receiving the probe beam after it has been reflected from the surface of the substrate, said detector means for measuring the intensity of various rays as a function of position within the reflected probe beam, with the position of the rays within said reflected probe beam corresponding to specific angles of incidence with respect to said surface; and
processor means for determining the thickness of the thin film layer based upon the angular dependent intensity measurements made by the detector means.

6. An apparatus for measuring the thickness of a thin film layer on the surface of a substrate comprising:
means for generating a probe beam of radiation;
means for focusing said probe beam to a diameter of about one micron or less onto the surface of the substrate such that various rays within the focused probe beam create a spread of angles of incidence with respect to said surface;
detector means for receiving the probe beam after it has been reflected from the surface of the substrate, said detector means for measuring the intensity of various rays as a function of position within the reflected probe beam, with the position of the rays within said reflected probe beam corresponding to specific angles of incidence with respect to said surface; and
processor means for determining the thickness of the thin film layer based upon the angular dependent intensity measurements made by the detector means.

7. An apparatus for measuring the thickness of a thin film layer on the surface of a substrate comprising:
means for generating a probe beam of radiation;
means for focusing said probe beam onto the surface of the substrate such that various rays within the focused probe beam create a spread of angles of incidence with respect to said surface and wherein the light in said probe beam is linearly polarized prior to being focused by said focusing means and wherein said probe beam is focused substantially normal to the surface of the substrate such that light rays incident on the sample surface have substantial components of S and P polarized light with respect to the plane of incidence at the sample surface;
detector means for receiving the probe beam after it has been reflected from the surface of the substrate, said detector means for measuring the intensity of various rays as a function of position within the reflected probe beam, with the position of the rays within said reflected probe beam corresponding to specific angles of incidence with respect to said surface; and
processor means for determining the thickness of the thin film layer based upon the angular dependent intensity measurements made by the detector means.

8. An apparatus as recited in claim 7 wherein said detector means isolates and measures the angular dependent intensity of the S and P polarized components of said focused incident probe beam and said processor means utilizes the angular dependent intensity measurement of the S and P polarized light to determine the thickness of the thin film layer.

9. An apparatus as recited in claim 8 wherein said detector means includes means for measuring the intensity of the reflected probe beam along two orthogonal axes oriented in a manner to isolate the angular dependent intensity of the S and P polarized components of said focused incident probe beam.

10. An apparatus for measuring the thickness of a thin film layer on the surface of a substrate comprising:
means for generating a probe beam of radiation;

means for focusing said probe beam onto the surface of the substrate such that various rays within the focused probe beam create a spread of angles of incidence with respect to said surface;

detector means for receiving the probe beam after it has been reflected from the surface of the substrate, said detector means for measuring the intensity of various rays as a function of position within the reflected probe beam, with the position of the rays within said reflected probe beam corresponding to specific angles of incidence with respect to said surface; and processor means for determining the thickness of the thin film layer based upon the angular dependent intensity measurements made by the detector means and wherein said processor means determines the thickness of the thin film layer using a mathematical model which relates the angular dependent intensity measurements made by the detector means, angle of incidence, polarization of the rays of the focused incident probe beam and layer thickness.

11. An apparatus for measuring the thickness of a thin film layer on the surface of a substrate comprising:

means for generating a probe beam of radiation;

means for focusing said probe beam onto the surface of the substrate such that various rays within the focused probe beam create a spread of angles of incidence with respect to said surface;

detector means for receiving the probe beam after it has been reflected from the surface of the substrate, said detector means for measuring the intensity of various rays as a function of position within the reflected probe beam, with the position of the rays within said reflected probe beam corresponding to specific angles of incidence with respect to said surface; and processor means for determining the thickness of the thin film layer based upon the angular dependent intensity measurements made by the detector means and wherein said detector means further functions to measure the total power of the reflected probe beam and wherein said processor means determines the thickness of the thin film layer based upon both the angular dependent intensity measurements and the total reflected power measurements made by the detector means.

12. An apparatus as recited in claim 11 wherein said processor utilizes the angular dependent intensity measurements to approximate the thickness of the thin film layer and utilizes the total reflected power measurement to reduce the uncertainty of the result.

13. An apparatus for measuring the thickness of a thin film layer on the surface of a substrate comprising:

means for generating a probe beam of linearly polarized radiation;

lens means for focusing said probe beam substantially normal to the surface of the substrate such that various rays within the focused probe beam create a spread of angles of incidence with respect to said surface and such that light rays incident on the sample surface have substantial components of S and P polarized light with respect to the plane of incidence at the sample surface;

detector means for receiving the probe beam after it has been reflected from the surface of the substrate, said detector means for measuring the intensity of various rays as a function of position within the reflected probe beam in a manner to isolate the S and P polarization components, with the position of the rays within said reflected probe beam corresponding to specific angles of incidence with respect to said surface; and processor means for determining the thickness of the thin film layer based upon the angular dependent intensity measurements of the S and P polarized light made by the detector means.

14. An apparatus as recited in claim 13 wherein said detector means includes means for measuring the intensity of the reflected probe beam along two orthogonal axes oriented in a manner to isolate the angular dependent intensity of the S and P polarized components of said focused incident probe beam.

15. An apparatus as recited in claim 13 wherein said focused incident probe beam has at least one ray having a substantial component of P polarized light inclined near Brewster's angle with respect to the thin film layer and wherein said processor means further functions to determine information as to the index of refraction of said thin film layer based on the measurement of the intensity of reflected P polarized light incident on the sample near Brewster's angle.

16. An apparatus as recited in claim 13 wherein said incident probe beam is focused to a diameter of about one micron or less on the surface of the substrate.

17. An apparatus for measuring the thickness of a thin film layer on the surface of a substrate comprising:

means for generating a probe beam of radiation;

lens means for focusing said probe beam onto the surface of the substrate, such that various rays within the focused probe beam create a spread of angles of incidence with respect to said surface;

detector means for receiving the probe beam after it has been reflected from the surface of the substrate, said detector means for measuring the intensity of various rays as a function of position within the reflected probe beam, with the position of the rays within said reflected probe beam corresponding to specific angles of incidence with respect to said surface; and processor means for determining the thickness of the thin film layer using a mathematical model which relates the angular dependent intensity measurements made by the detector means, angle of incidence, polarization of the rays of the focused incident probe beam and layer thickness.

18. An apparatus as recited in claim 17 wherein said lens means has a numerical aperture of at least 0.5 and said probe beam is focused substantially normal to the surface of the substrate.

19. An apparatus as recited in claim 17 wherein said incident probe beam is focused to a diameter of about one micron or less on the surface of the substrate.

20. An apparatus for measuring the thickness of a thin film layer on the surface of a substrate comprising:

means for generating a probe beam of radiation;

lens means for focusing said probe beam onto the surface of the substrate such that various rays within the focused probe beam create a spread of angles of incidence with respect to said surface;

first detector means for receiving the probe beam after it has been reflected from the surface of the substrate, said first detector means for measuring the intensity of various rays as a function of position within the reflected probe beam, with the position of the rays within said reflected probe beam corresponding to specific angles of incidence with respect to said surface;

second detector means for receiving the probe beam after it has been reflected from the surface of the substrate, said second detector means for measuring the total power of the reflected probe beam; and processor means for determining the thickness of the thin film layer based upon both the angular dependent intensity measurements made by the first detector means and the total reflected power measured by the second detector means.

21. An apparatus as recited in claim 20 wherein said processor utilizes the angular dependent intensity measurements to approximate the thickness of the thin film layer and utilizes the total reflected power to reduce the uncertainty of the result.

22. An apparatus as recited in claim 20 wherein said lens means has a numerical aperture of at least 0.5 and said probe beam is focused substantially normal to the surface of the substrate.

23. An apparatus as recited in claim 20 wherein said incident probe beam is focused to a diameter of about one micron or less on the surface of the substrate.

24. An apparatus for evaluating parameters of a sample which includes a thin film layer on the surface of a substrate comprising:

means for generating a probe beam of radiation;

lens means for focusing said probe beam onto the surface of the sample such that various rays within the focused probe beam create a spread of angles of incidence with respect to said surface;

detector means for receiving the probe beam after it has been reflected from the surface of the substrate, said detector means for measuring the intensity of various rays as a function of position within the reflected probe beam, with the position of the rays within said reflected probe beam corresponding to specific angles of incidence with respect to said surface; and processor means for determining parameters of the sample including the thickness of the thin film layer and the index of refraction of the thin film layer or the substrate based upon the angular dependent intensity measurements made by the detector means and wherein the light in said probe beam is linearly polarized prior to being focused by said lens means and wherein sad probe beam is focused substantially normal to the surface of the substrate such that light rays incident on the sample surface have substantial components of S and P polarized light with respect to the plane of incidence at the sample surface.

25. An apparatus as recited in claim 24 wherein said detector means isolates and measures the angular dependent intensity of the reflected S and P polarized components of said focused incident probe beam and said processor means utilizes the angular dependent intensity measurement of the S and P polarized light to determine the parameters of the sample.

26. An apparatus as recited in claim 25 wherein said detector means includes means for measuring the intensity of the reflected probe beam along two orthogonal axes oriented in a manner to isolate the angular dependent intensity of the S and P polarized components of said focused incident probe beam.

27. An apparatus as recited in claim 25 wherein said focused incident probe beam has at least one ray having a substantial component of P polarized light inclined near Brewster's angle with respect to the thin film layer and wherein said processor means further functions to determine information as to the index of refraction of said thin film layer based on the measurement of the intensity of reflected P polarized light incident on the sample near Brewster's angle.

28. An apparatus for evaluating parameters of a sample which includes a thin film layer on the surface of a substrate comprising:

means for generating a probe beam of radiation;

lens means for focusing said probe beam to a diameter of about one micron or less onto the surface of the sample such that various rays within the focused probe beam create a spread of angles of incidence with respect to said surface;

detector means for receiving the probe beam after it has been reflected from the surface of the substrate, said detector means for measuring the intensity of various rays as a function of position within the reflected probe beam, with the position of the rays within said reflected probe beam corresponding to specific angles of incidence with respect to said surface; and processor means for determining parameters of the sample including the thickness of the thin film layer and the index of refraction of the thin film layer or the substrate based upon the angular dependent intensity measurements made by the detector means.

29. An apparatus for measuring the thickness of a thin film layer on the surface of a substrate comprising:

means for generating a probe beam of radiation;

lens means for focusing said probe beam onto the surface of the substrate such that various rays within the focused probe beam create a spread of angles of incidence with respect to said surface and wherein said lens means has a numerical aperture of at least 0.5 and said probe beam is focused substantially normal to the surface of the substrate;

detector means for receiving the reflected probe beam, said detector means for measuring the interference effected created by the interaction between the rays of the probe beam reflecting off the thin film layer and the upper surface of the underlying substrate as a function of position within the reflected probe beam, with the position of the interference effects within said reflected probe beam corresponding to specific angles of incidence with respect to said surface; and processor means for determining the thickness of the thin film layer based upon the angular dependent interference effects measured made by the detector means.

30. An apparatus for measuring the thickness of a thin film layer on the surface of a substrate comprising;

means for generating a probe beam of radiation;

lens means for focusing said probe beam to a diameter of about one micron or less onto the surface of the substrate such that various rays within the focused probe beam create a spread of angles of incidence with respect to said surface;

detector means for receiving the reflected probe beam, said detector means for measuring the interference effects created by the interaction between the rays of the probe beam reflecting off the thin film layer and the upper surface of the underlying substrate as a function of position within the reflected probe beam, with the position of the interference effects within said reflected probe beam corresponding to specific angles of incidence with respect to said surface; and processor means for determining the thickness of the thin film layer based upon the angular dependent interference effects measured made by the detector means.

31. An apparatus as recited in claims 29 or 30 wherein said interference effects in said reflected probe beam are in the form of intensity variations.

32. An apparatus as recited in claims 1, 2, 4, 5, 6, 7, 10, 11, 17, 24, 28, 29 or 30 wherein said detector means measures the intensity across the reflected probe beam at a plurality of discrete points, from the center of the reflected probe beam to the outer edge thereof.

33. A method of measuring the thickness of a thin film layer on the surface of a substrate comprising the steps of:

generating a probe beam of radiation;
focusing the probe beam substantially normal onto the surface of the substrate such that various rays within the focused probe beam create a spread of angles of incidence with respect to said surface;
measuring the intensity of various rays as a function of position within the reflected beam with the position of the rays within said reflected probe beam corresponding to specific angles of incidence with respect to said surface; and
determining the thickness of the thin film layer based upon the angularly dependent intensity measurements.

34. A method of measuring the thickness of a thin film layer on the surface of a substrate comprising the steps of:

generating a probe beam of radiation;
focusing the probe beam on the surface of the substrate such that various rays within the focused probe beam create a spread of angles of incidence with respect to said surface wherein said incident probe beam is focused in a manner such that it includes at least one ray that is substantially normal to the surface of the substrate;
measuring the intensity of various rays as a function of position within the reflected beam with the position of the rays within said reflected probe beam corresponding to specific angles of incidence with respect to said surface; and
determining the thickness of the thin film layer based upon the angularly dependent intensity measurements.

35. A method of measuring the thickness of a thin film layer on the surface of a substrate comprising the steps of:

generating a probe beam of radiation;
focusing the probe beam on the surface of the substrate such that various rays within the focused probe beam create a spread of angles of incidence with respect to said surface wherein said incident probe beam is focused in a manner to include at least one ray that is inclined near Brewster's angle with respect to either the thin film layer or the substrate;
measuring the intensity of various rays as a function of position within the reflected beam with the position of the rays within said reflected probe beam corresponding to specific angles of incidence with respect to said surface; and determining the thickness of the thin film layer based upon the angularly dependent intensity measurements.

36. A method of measuring the thickness of a thin film layer on the surface of a substrate comprising the steps of:

generating a probe beam of radiation;
focusing the probe beam on the surface of the substrate such that various rays within the focused probe beam create a spread of angles of incident with respect to said surface wherein the incident probe beam is focused in a manner such that the variation in the angle of incidence of the rays with respect to the substrate is at least 30 degrees;
measuring the intensity of various rays as a function of position within the reflected beam with the position of the rays within said reflected probe beam corresponding to specific angles of incidence with respect to said surface; and
determining the thickness of the thin film layer based upon the angularly dependent intensity measurements.

37. A method of measuring the thickness of a thin film layer on the surface of a substrate comprising the steps of:

generating a probe beam of radiation;
focusing the probe beam to a diameter of about one micron or less on the surface of the substrate such that various rays within the focused probe beam create a spread of angles of incidence with respect to said surface;
measuring the intensity of various rays as a function of position within the reflected beam with the position of the rays within said reflected probe beam corresponding to specific angles of incidence with respect to said surface; and
determining the thickness of the thin film layer based upon the angularly dependent intensity measurements.

38. A method of measuring the thickness of a thin film layer on the surface of a substrate comprising the steps of:

generating a probe beam of radiation;
focusing the probe beam on the surface of the substrate such that various rays within the focused probe beam create a spread of angles of incidence with respect to said surface and wherein the light in said probe beam is linearly polarized prior to being focused and wherein said probe beam is directed substantially normal to the surface of the substrate such that the light incident on said substrate includes substantial components of S and P polarized light with respect to the plane of incidence at the sample surface;
measuring the intensity of various rays as a function of position within the reflected beam with the position of the rays within said reflected probe beam corresponding to specific angles of incidence with respect to said surface; and
determining the thickness of the thin film layer based upon the angularly dependent intensity measurements.

39. A method as recited in claim 38 further including the steps of:

isolating the angular dependent intensity variations of the S and P polarized components of said focused incident probe beam; and determining the thickness of the thin film layer utilizing the angular dependent intensity measurement of the S and P polarized light.

40. A method as recited in claim 39 wherein said isolation step is performed by measuring the intensity of the reflected probe beam along two orthogonal axes oriented in a manner to isolate the angular dependent intensity variations of the S and P polarized components of said focused incident probe beam.

41. A method as recited in claim 39 wherein said incident probe beam has at least one ray having a substantial component of P polarized light inclined near Brewster's angle with respect to the thin film layer and further including the step of determining the index of refraction of said thin film layer based on the measurement of the intensity of reflected P polarized light incident on the sample near Brewster's angle.

42. A method of measuring the thickness of a thin film layer on the surface of a substrate comprising the steps of:

generating a probe beam of radiation;

focusing the probe beam on the surface of the substrate such that various rays within the focused probe beam create a spread of angles of incidence with respect to said surface;

measuring the intensity of various rays as a function of position within the reflected beam with the position of the rays within said reflected probe beam corresponding to specific angles of incidence with respect to said surface; and determining the thickness of the thin film layer based upon the angularly dependent intensity measurements and wherein the thickness of the thin film is calculated using a mathematical model which relates the angular dependent intensity measurements, angle of incidence and polarization of the rays of the focused incident probe beam with layer thickness.

43. A method of measuring the thickness of a thin film layer on the surface of a substrate comprising the steps of:

generating a probe beam of radiation;

focusing the probe beam on the surface of the substrate such that various rays within the focused probe beam create a spread of angles of incidence with respect to said surface;

measuring the intensity of various rays as a function of position within the reflected beam with the position of the rays within said reflected probe beam corresponding to specific angles of incidence with respect to said surface;

measuring the total power of the reflected probe beam; and determining the thickness of the thin film layer based upon both the angular dependent intensity measurements and the total reflected power.

44. A method as recited in claim 43 wherein the angular dependent intensity measurements are utilized to approximate the thickness of the thin film layer and the total reflected power measurement is utilized to reduce the uncertainty of the result.

* * * * *